United States Patent [19]

Kobayashi et al.

[11] Patent Number: 5,059,345

[45] Date of Patent: Oct. 22, 1991

[54] OPTICALLY ACTIVE COMPOUND AND CHIRAL LIQUID CRYSTAL COMPOSITION CONTAINING THE SAME

[75] Inventors: Shogo Kobayashi, Tokyo; Shigeki Ishibashi, Houya; Toshio Horie, Iruma; Shinji Tsuru, Higashimurayama; Kouzaburou Nakamura, Tokyo; Tohru Maruno, Mito, all of Japan

[73] Assignee: Nippon Telegraph and Telephone Corporation, Tokyo, Japan

[21] Appl. No.: 266,832

[22] Filed: Nov. 3, 1988

[30] Foreign Application Priority Data

| Nov. 6, 1987 | [JP] | Japan | 62-280456 |
| Nov. 6, 1987 | [JP] | Japan | 63-280458 |
| Jun. 3, 1988 | [JP] | Japan | 63-136792 |
| Jun. 3, 1988 | [JP] | Japan | 63-136793 |
| Jun. 3, 1988 | [JP] | Japan | 63-136794 |
| Aug. 29, 1988 | [JP] | Japan | 63-214632 |
| Aug. 30, 1988 | [JP] | Japan | 63-216126 |
| Oct. 11, 1988 | [JP] | Japan | 63-255437 |
| Oct. 11, 1988 | [JP] | Japan | 63-255438 |

[51] Int. Cl.$^5$ .................. C09K 19/34; C07D 239/02; C07C 39/12; C07C 69/76

[52] U.S. Cl. .................. 252/299.61; 252/299.63; 252/299.65; 252/299.67; 544/298; 544/335; 568/731; 568/744; 568/747; 560/59; 560/65; 560/73; 560/102; 560/108; 560/109; 359/104

[58] Field of Search .................. 252/299.01, 299.61, 252/299.63, 299.65, 299.67, 299.64, 299.66; 350/350 S; 560/59, 65, 73, 102, 108, 109, 8; 544/298, 335, 242; 568/731, 732, 744, 747

[56] References Cited

U.S. PATENT DOCUMENTS

| 4,576,732 | 3/1986 | Isogai et al. | 252/299.65 |
| 4,596,667 | 6/1986 | Inukai et al. | 252/299.65 |
| 4,613,209 | 9/1986 | Goodby et al. | 350/350 S |
| 4,647,398 | 3/1987 | Sato et al. | 252/299.65 |
| 4,676,925 | 6/1987 | Inoue et al. | 252/299.65 |
| 4,780,241 | 10/1988 | Furuawa et al. | 252/299.63 |
| 4,834,907 | 5/1959 | Inoue et al. | 252/299.65 |

FOREIGN PATENT DOCUMENTS

136725 4/1985 European Pat. Off. .
115829 10/1975 Fed. Rep. of Germany .
(List continued on next page.)

OTHER PUBLICATIONS

Goodby et al., J. Amer. Chem. Soc., vol. 108, pp. 4736–4742 (Aug. 1956).
(List continued on next page.)

*Primary Examiner*—John S. Maples
*Assistant Examiner*—Philip Tucker
*Attorney, Agent, or Firm*—Frishauf, Holtz, Goodman et al.

[57] ABSTRACT

An optically active compound represented by the general formula (I) of:

$$R-Z-COO-(Ph)_k-Ph(Y)-CO-(CH_2)_m C^*HE \quad (1)$$
$$\phantom{R-Z-COO-(Ph)_k-Ph(Y)-CO-(CH_2)_m}L$$

In the general formula (I); R is an alkyl or alkoxy group having 4 to 22 carbon atoms; Z is the one selected from the group consisting of —Ph—, —Ph(X)—, —Ph—Ph—, Ph(X)—Ph—, —Ph—cy—, —Ph(X)—cy— and —py—Ph— is a 1,4-substituted phenylene group; —Ph—Ph— is a 4,4'-substituted diphenylene group; —cy— is a trans-1,4-cyclohexane group, —py is 2,5-substituted pyrimide group; X is a halogen atom at the ortho-position to R; k is zero or 1, Y is the one selected from the group consisting of H, OH, halogen atoms and methyl group; C* is an asymmetric carbon atom; E is the one selected from the group consisting of methyl group, halogen atoms and CF$_3$; L is an alkyl, aryl or aralkyl group having not more than 10 carbon atoms; and m is an integer of zero to 6 where m takes zero when Y is H and Z is —Ph— or —Ph—Ph—. The optically active compound is usable as an ingredient for a liquid crystal composition which has high spontaneous polarization, exhibits the Sc* phase (chiral smectic C liquid crystalline phase) in a wide temperature range and high speed response.

7 Claims, 3 Drawing Sheets

FOREIGN PATENT DOCUMENTS

| | | |
|---|---|---|
| 2429093 | 5/1978 | Fed. Rep. of Germany . |
| 2561657 | 9/1985 | France . |
| 61-63633 | 4/1986 | Japan . |
| 1453463 | 10/1976 | United Kingdom . |
| 2199826 | 7/1988 | United Kingdom . |

OTHER PUBLICATIONS

Malthete et al., Tetrahedron, vol. 37(16), pp. 2815–2821 (1981).

Demus et al., (ed.), Flussige Kristable in Tabellen, p. 70 (1974).

Demus et al., (ed.), Flassige Kristalle in Tabellen II, p. 122 (1984).

N. A. Clark et al., "Submicrosecond Sistable Electro-Optic Switching in Liquid Crystals", Appl. Phys. Lett., 36 899 (1980).

J. W. Goodby et al., J. Am. Chem. Soc., 108, pp. 4736 to 4742 (1986).

Ichihashi et al., 13th Japanese Conference on Liquid Crystals, Oct. 16 to 18 (1987), pp. 50 to 51.

A : n-C$_{10}$H$_{21}$O-Ph-Ph-COO-Ph(OH)-CO-ĊH(Me)-Et
B : n-C$_{12}$H$_{25}$O-Ph-COO-Ph-O-CH$_2$-ĊH(Me)-Et

C : n-C₁₀H₂₁-O-Ph-Ph-COO-Ph(OH)-CO-ĊH(Me)-Et
D : n-C₈H₁₇-O-Ph-COO-Ph-COO CH₂ ĊH(Me)-Et

E: n-C$_{10}$H$_{21}$-O-Ph-Ph-COO-Ph(OH)-CO-CH(Me)-Et
F: n-C$_8$H$_{17}$-O-Ph-COO-Ph(OH)-CO-CH(Me)-Et

OPTICALLY ACTIVE COMPOUND AND CHIRAL LIQUID CRYSTAL COMPOSITION CONTAINING THE SAME

BACKGROUND OF THE INVENTION

1. Field of the Invention

The present invention relates to optically active liquid crystal materials and liquid crystal compositions containing the optically active liquid crystal materials.

Throughout the specification, the "liquid crystal material" includes not only materials which exhibit the liquid crystal phases by themselves, but also materials which are usable as ingredients in liquid crystal compositions although not detected to exhibit the liquid crystal phases by themselves.

2. Prior Art Statement

Liquid crystal displays have advantages that they are actuated by low electric voltage, that they consume only little electric power, that they are fabricated into thin layer forms, and that they are relatively light in weight. Making use of these advantages, liquid crystal display devices are applied for use in desk electric calculators, watches and televisions. Nematic liquid crystals have hitherto been widely used as the materials for such display elements. However, nematic liquid crystals are detrimental in that the response speeds thereof are low, i.e. in the order of several tens milliseconds. In order to avoid the disadvantage of the nematic liquid crystals, it has been proposed to use ferroelectric liquid crystals in the display system, for example, by N. A. Clark et al., "Submicrosecond Bistable Electro-Optic Switching in Liquid Crystals", Appl. Phys. Lett., 36, 899 (1980). In the display system proposed by this prior art reference, the chiral smectic C liquid-crystalline phase (hereinafter referred to as "Sc* phase") of a ferroelectric liquid crystal is utilized. It is required that the ferroelectric liquid crystal materials used for such purpose exhibit the Sc* phase in a wide temperature range, have high spontaneous polarization and low rotational viscosity. However, the known ferroelectric liquid crystal compounds are detrimantal in that they exhibit the Sc* phase in only a narrow temperature range and that the spontaneous polarization thereof is low. Particularly, the compounds having azomethine groups are inferior in chemical stability and thus cannot be applied for practical use. Accordingly, there is an increasing demand for a ferroelectric liquid crystal which has chemical stability and high spontaneous polarization and which exhibits the Sc* phase in a wide temperature range.

In order to apply ferroelectric liquid crystals in a practical electro-optic switching element, it is required to control the Sc* temperature range and the electro-optic characteristics thereof, such as spontaneous polarization, viscosity, helical twist and tilt angle, within proper ranges. To satisfy the requirement, it has been tried to use a mixture containing a compound having high spontaneous polarization or inducing high spontaneous polarization, a compound having a low viscosity, compounds having reverse helical twists, and compounds which exhibit the Sc or Sc* phase in a wide temperature range. It becomes thus necessary to investigate a number of materials to find out the optimum condition for the appropriate characteristics, such materials to be investigated include:

(1) Materials having or inducing high spontaneous polarization;
(2) Compounds which can unloose or release the helical twist by the addition thereof in a small quantity; and
(3) Liquid crystal compounds exhibiting the smectic C phase in a wide temperature range.

It is thus demanded to find a number of liquid crystal materials having various properties and being capable of constituting the liquid crystal compositions.

OBJECTS AND SUMMARY OF THE INVENTION

Accordingly, a primary object of this invention is to provide a novel ferroelectric liquid crystal material which is chemically stable and exhibits the Sc* phase in a wide temperature range and which has rapid response characteristics.

Another object of this invention is to provide a liquid crystal material including an optically active group.

A further object of this invention is to provide a novel chiral liquid crystal composition.

The optically active compound provided by this invention is represented by the following general formula (I) of:

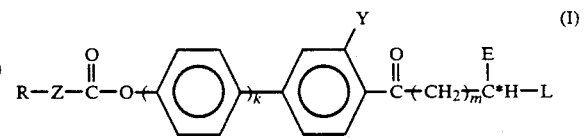

wherein R is an alkyl or alkoxy group having 4 to 22 carbon atoms; Z is the one selected from the group consisting of

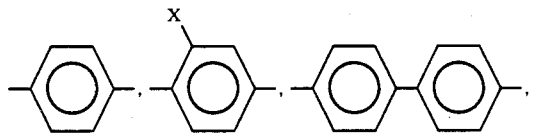

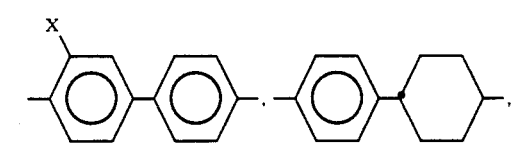

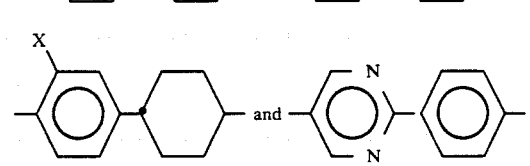

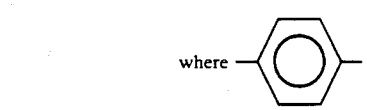

represents 1,4-phenylene group:

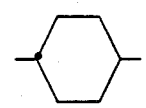

represents trans-1,4-cyclohexane group: X is a substituent selected from halogen atoms; k is zero or 1; Y is the one selected from hydrogen atom, hydroxyl group, halogen atoms and methyl group; C* represents an asymmetric carbon atom; E is the one selected from the group consisting of methyl group, halogen atoms and CF$_3$; L is an alkyl, aryl or aralkyl group having not more than 10 carbon atoms; and m is an integer of from 0 to 6 where m takes O when Y is a hydrogen atom and Z is

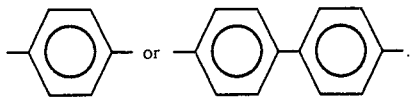

The chiral liquid crystal composition provided by this invention is characterized in that it is a mixture of liquid crystal compounds containing at least one of the optically active compounds represented by the general formula (I) of:

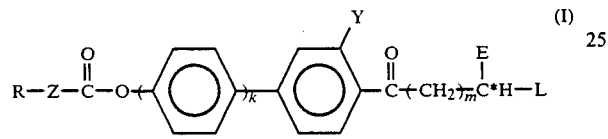

wherein R, Z, k, Y, C*, E, L and m are the same as defined above.

A variety of optically active compounds may be synthesized by properly selecting R, Z, k, Y, E, L and m in the general formula (I).

Liquid crystal compounds, other than the optically active compounds represented by the general formula (I), which may be added to form the liquid crystal composition of this invention include the following ferroelectric liquid crystal compounds and the following non-ferroelectric liquid crystal compounds which do not contain asymmetric carbon atom. In the following lists, Ph stands for a 1,4-substituted phenylene group, Ph—Ph stands for a 4,4'-substituted diphenylene group, Py stands for 2,5-substituted pyrimidine ring, C* stands for an asymmetric carbon atom, Alk stands for a straight chain alkyl group having 6 to 14 carbon atoms, Alk' stands for an alkyl having 2 to 6 carbon atoms or isobutyl group, Me stands for a methyl group and Et stands for an ethyl group.

(A) Ferroelectric Liquid Crystal Compounds

Alk—O—Ph—Ph—COO—CH$_2$—C*H(Me)—Et,
Alk—O—Ph—COO—Ph—CH$_2$—C*H(Me)—Et,
Alk—O—Ph—COO—Ph—O—CH$_2$—C*H-(Me)—Et,
Et—C*H(Me)—C$_5$H$_{10}$—O—Ph—COO—Ph—O—Alk,
Alk—O—Ph—COO—Ph—Ph—O—CH$_2$—C*H-(Me)—Et,
Alk—O—Ph—Ph—OCO—Ph—CH$_2$—C*H-(Me)—Et,
Alk—O—Ph—Ph—OCO—Ph—CH$_2$—C*H-(Me)—Et,
Alk—O—Ph—OCO—Ph—Ph—O—CH$_2$—C*H-(Me)—Et,
Alk—O—Ph—OCO—Ph—OCO—Ph—O—CH$_2$—C*H(Me)—Et,
Alk—O—Ph—OCO—Ph—OCO—Ph—O—C$_3$H$_6$—C*H(Me)—Et,
Alk—O—Py—Ph—O—C$_2$H$_4$—C*H(Me)—Et,
Alk—O—Py—Ph—O—CH$_2$—C*H(Me)—Et,
Alk—O—Py—Ph—O—C$_3$H$_6$—C*H(Me)—Et,
Alk—O—Py—Ph—O—C$_5$H$_{10}$—C*H(Me)—Et,
Alk—O—Ph—COO—Ph—COO—C*H(Me)—CH$_2$—O—Alk',
Alk—O—Ph—Ph—COO—Ph—COO—C*H(Me)—CH$_2$—O—Alk',
Alk—O—Ph—COO—Ph—Ph—COO—C*H(Me)—CH$_2$—O—Alk',
Alk—O—Ph—COO—Ph—OCO—C*H(Me)—O—Alk',
Alk—O—Ph—OCO—Ph—OCO—C*H(Me)—O—Alk',
Alk—O—Ph—Ph—COO—Ph—OCO—C*H(Me)—O—Alk',
Alk—O—Ph—Ph—OCO—Ph—OCO—C*H(Me)—O—Alk'.

(B) Non-Ferroelectric Liquid Crystal Compounds

Alk—O—Ph—COO—Ph—O—Alk'
Alk—O—Ph—COO—Ph—Alk'
Alk—Ph—COO—Ph—O—Alk'
Alk—COO—Ph—COO—Ph—Alk'
Alk—COO—Ph—COO—Ph—O—Alk'
Alk—O—Py—Ph—O—Alk'
Alk—O—Py—Ph—Alk',
Alk—Py—Ph—O—Alk',
Alk—Ph—Ph—COO—Ph—O—Alk',
Alk—O—Ph—Ph—COO—Ph—O—Alk',
Alk—O—Py—Ph—O—CO—Alk',
Alk—Py—Ph—OCO—Alk'.

BRIEF DESCRIPTION OF THE DRAWING

The above and other objects and advantages of the present invention will become more apparent upon reference to the following description and annexed drawings in which.

Figure 1:
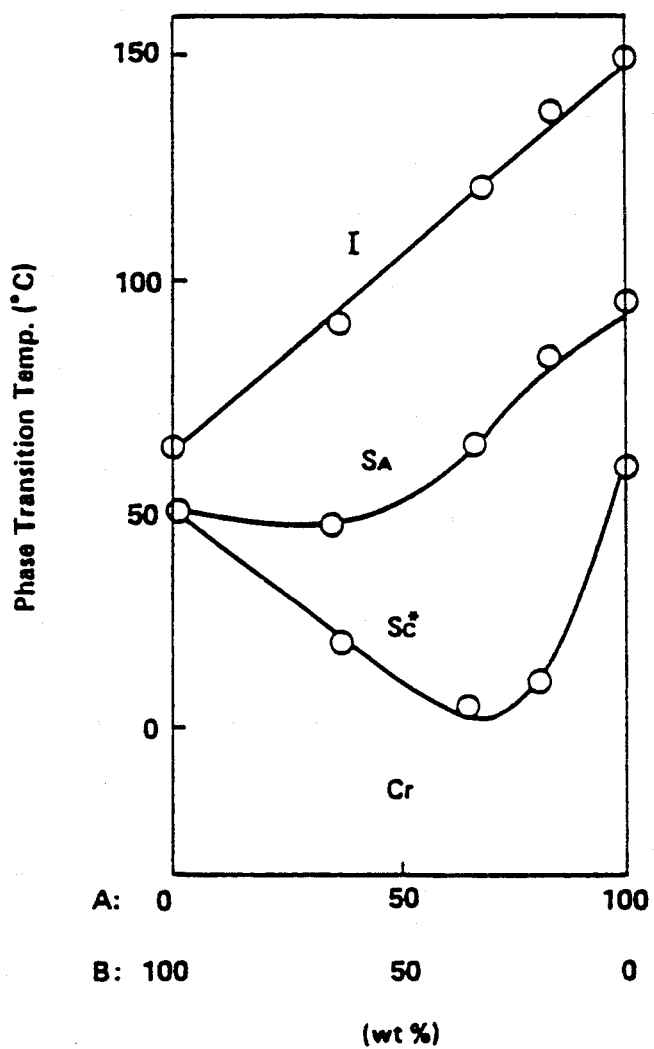
FIG. 1 is a phase diagram of a mixture of
n—C$_{10}$H$_{21}$—O—Ph—Ph—COO—Ph(OH)—CO—C*H(Me)—Et and
n—C$_{12}$H$_{25}$—O—Ph—COO—Ph—O—CH$_2$—C*H-(Me)—Et.
Figure 2:
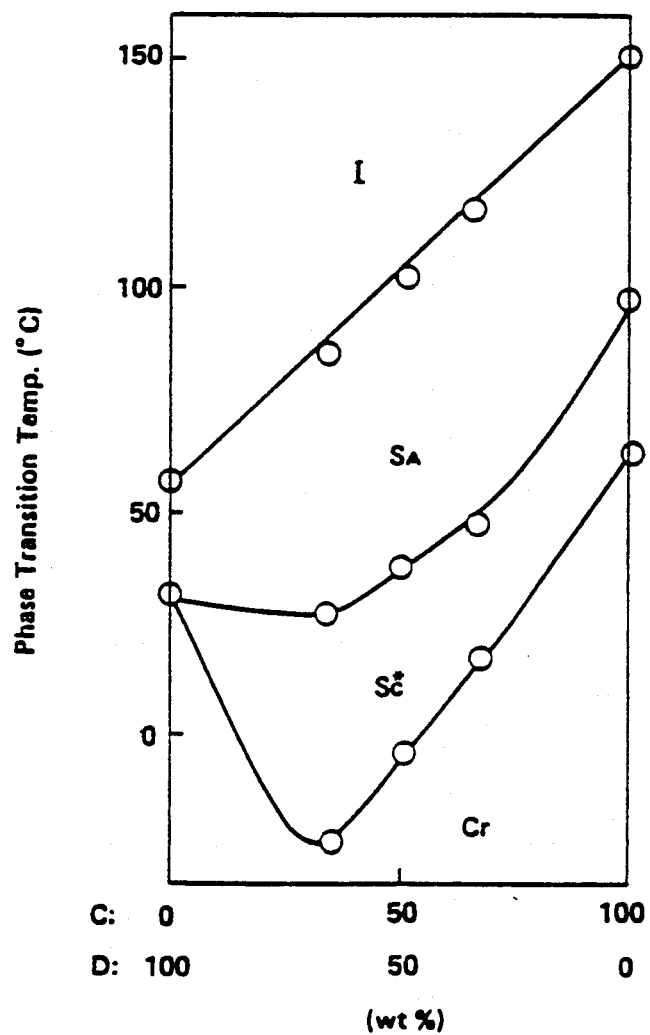
FIG. 2 is a phase diagram of a mixture of
n—C$_{10}$H$_{21}$—O—Ph—Ph—COO—Ph(OH)—CO—C*H(Me)—Et and
n—C$_8$H$_{17}$—O—Ph—COO—CH$_2$—C*H(Me)—Et.
Figure 3:
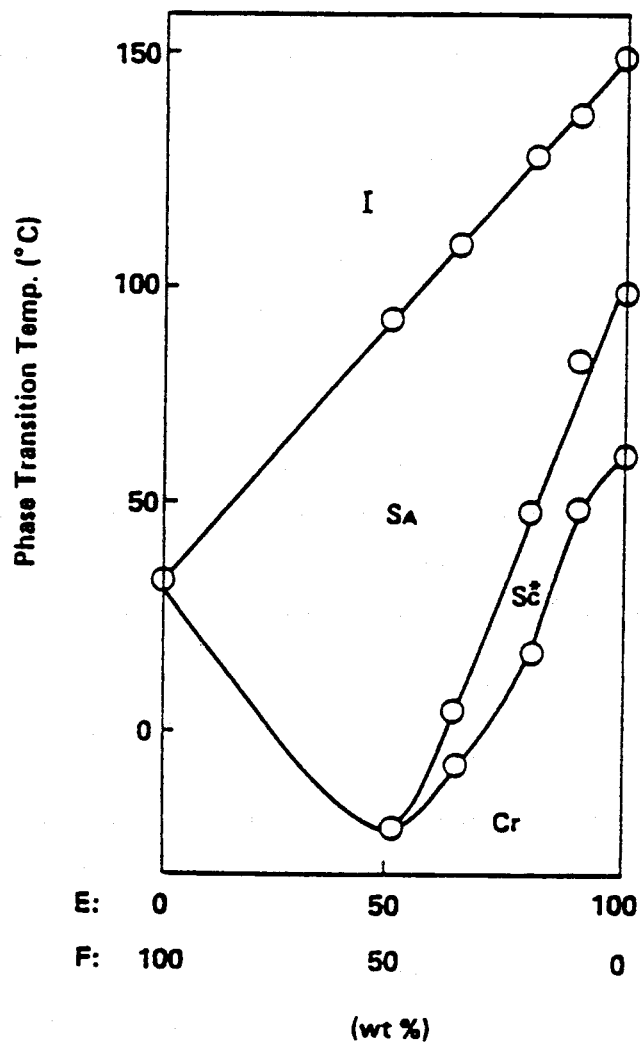
FIG. 3 is a phase diagram of a mixture of
n—C$_{10}$H$_{21}$—O—Ph—Ph—COO—Ph(OH)—CO—C*H(Me)—Et and
n—C$_8$H$_{17}$—O—Ph—COO—Ph(OH)—CO—C*H-(Me)—Et wherein Ph(OH) is a 1,4-substituted phenylene group having OH group at the ortho-position to the carbonyl group.

Throughout FIGS. 1 to 3, the ordinate indicates the phase transition temperature and the abscissa indicates the mixing ratio (wt %); and Cr stands for the crystalline phase, Sc* stands for the chiral smectic C liquid-crystalline phase, S$_A$ stands for the smectic A phase, and I stands for the isotropic liquid phase.

DESCRIPTION OF THE INVENTION

The first aspect of this invention resides in the provision of a ferroelectric liquid crystal exhibiting high spontaneous polarization by binding the molecular structure of —Ph—COO—Ph, —PhCOO—Ph—Ph— or —Ph—Ph—CO—Ph (hereinafter referred to as "core") directly with a carbonyl group which is bond directly with an asymmetric carbon atom.

The spontaneous polarization of a ferroelectric liquid crystal is induced by the dipole perpendicular to the molecular axis of the liquid crystal. Almost all of the known ferroelectric liquid crystals utilize the dipoles of esters or ethers. Ferroelectric liquid crystals having higher dipoles than dipoles of esters and ethers are made known by J. W. Goodby et al., J. Am. Chem. Soc., 108, pp 4736 to 4742 (1986), and S. Saito et al., Japanese Patent Application Laying Open for Public Inspection (KOKAI) No. 61-63633. However, these references do not disclose the spontaneous polarization of a ferroelectric liquid crystal having a carbonyl group. Anyway, spontaneous polarization of the liquid crystals disclosed by these prior art references are not so high since the carbonyl group and the asymmetric carbon atom are bound at separated positions. The following Table will be given to reveal that a compound having a carbonyl group bound directly with an asymmetric carbon atom has a higher polarization than those of compounds having intervening methylene or ethylene groups between the carbonyl group and the asymmetric carbon atom.

| Compound | Spontaneous Polarization (nC/cm$^2$) |
| --- | --- |
| $C_8H_{17}O$-Ph-Ph-COO-Ph-CO—$(C_2H_4)$—$C^*H(Me)$-Et | 4 |
| $C_8H_{17}O$-Ph-Ph-COO-Ph-CO—$CH_2$—$C^*H(Me)$-Et | 3 |
| $C_8H_{17}O$-Ph-Ph-COO-Ph-CO—$C^*H(Me)$-Et | 53 |

The spontaneous polarization was measured at a temperature below 10° C. from the upper limit of the Sc* phase.

The change in interrelationship between the dipole moment and the spontaneous polarization by changing the ether bond or ester bond positioned between the core and the asymmetric carbon atom to a carbonyl bond will be shown below. The data for the compounds having ether and ester bonds are found in the report by Ichihashi et al., 13th Japanese Conference on Liquid Crystals, Oct. 16 to 18 (1987), pp 50 to 51. The data for the compound having a carbonyl bond were measured by the inventor of this invention. The dipole moment and the spontaneous polarization of $C_8H_{17}O$—Ph—Ph—COO—Ph—A—$C^*H(Me)$—Hex (Hex stands for n-hexyl group) was measured.

| A | Dipole Moment (Debye) | Spontaneous Polarization nC/cm$^2$ |
| --- | --- | --- |
| —O— | 1.25 (PhOMe) | 41 |
| —COO— | 1.83 (PhCOOMe) | 70 |
| —CO— | 2.89 (PhCOMe) | 108 |

It will be seen that the spontaneous polarization increases with the increase in dipole moment, and the carbonyl bond exhibits the maximum spontaneous polarization.

The second aspect of this invention resides in the introduction of a hydroxyl group into a benzene ring of the core at the ortho-position to a carbonyl group bound directly with the core and an asymmetric carbon atom to provide a ferroelectric liquid crystal having higher spontaneous polarization, exhibiting the Sc* phase in a wider and lower temperature range.

It has been known to introduce a hydroxyl group to the core of a ferroelectric liquid crystal having an azomethine group. Since the azomethine group is easily hydrolysed, it has been investigated to introduce a hydroxyl group at the ortho-position of the benzene ring bound with the azomethine group to form intermolecular hydrogen bond between the nitrogen atom of the azomethine group and the hydroxy group for the purpose of improving the stability against hydrolysis. However, it has not been known to introduce hydroxyl groups in the ether or ester base ferroelectric liquid crystals that do not contain an azomethine group. It is considered that the hydroxyl group forms intermolecular hydrogen bond in these cores not only leading to considerable raise in melting point but also inducing disadvantageous raise in rotational viscosity.

According to this invention, hydroxyl group is introduced into a benzene ring at the ortho-position to carbonyl group so that an intramolecular hydrogen bond is formed to avoid the aforementioned disadvantage and to shift the temperature range for the Sc* phase to a lower temperature range. Formation of intramolecular hydrogen bond is confirmed by appearnace of an absorption peak at 1630 to 1640 cm$^{-1}$ due to the hydrogen bonded carbonyl group in the infrared absorption spectrum. By the introduction of hydroxyl group at the ortho-position to the carbonyl group, the spontaneous polarization of the resultant compound is also increased. This is because the dipole of carbonyl and the dipole of hydroxyl are oriented in the same direction by the formation of intramolecular hydrogen bond between the carbonyl group and the hydroxyl group.

The third aspect of this invention resides in the provision of liquid crystal materials which have various properties and can be used as ingredients of ferroelectric liquid crystal compositions having improved performance characteristics. In detail, the compounds represented by the general formula (I) include those which induce ferroelectricity by adding them to non-chiral liquid crystals having smectic C phase although they do not exhibit the Sc* phase by themselves. The compounds represented by the general formula (I) include those which have low spontanesous polarization per se but can release the helix of ferroelectric liquid crystals having high spontaneous polarization by the addition thereof. The compounds represented by the general formula (I) also include those having relatively small rotational viscosities due to the cyclohexane ring or pyrimidine ring contained therein.

The optically active compounds of this invention may generally been prepared by the following process.

In the following general formulae, R, Z, Y, E, L, C*, k and m stand for the same groups or atoms as defined in the general formula (I) above.

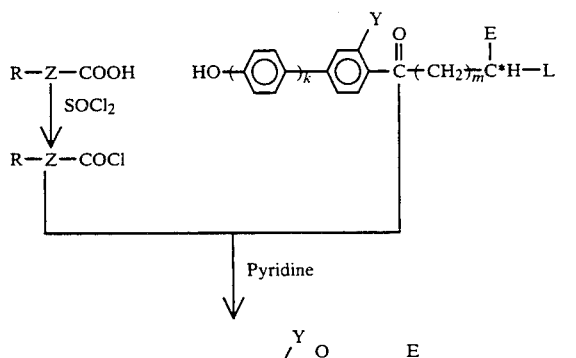

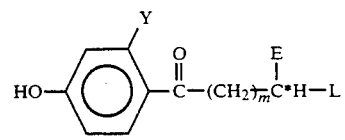

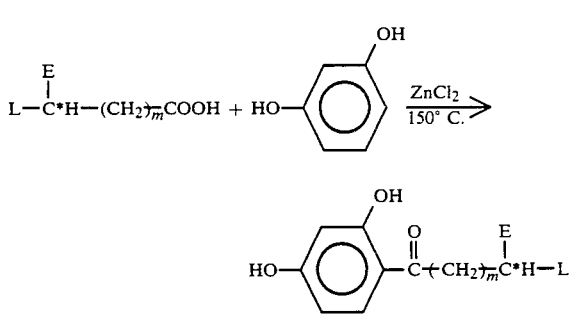

The compounds represented by the general formula (I) may be prepared by reacting acid halides with optically active substituted phenols.

Acid halides may be readily prepared by reacting corresponding carboxylic acids with thionyl chloride.

The optically active substituted phenols represented by the general formula set forth above wherein Y is a hydrogen atom or methyl group and k is zero, may be prepared through the Friedel-Crafts reaction as follows:

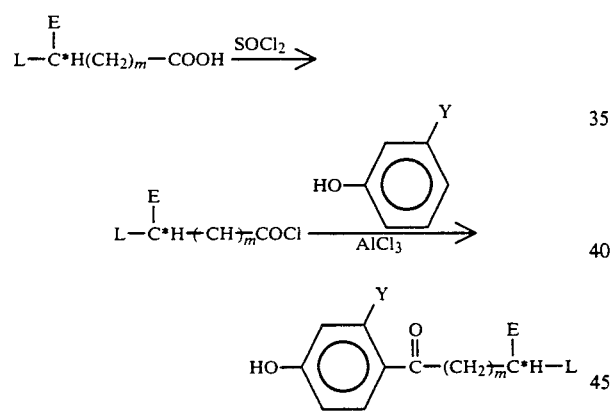

The optically active substituted phenols represented by the general formula set forth above wherein Y is a hologen atom and k is zero, may be prepared by the following process:

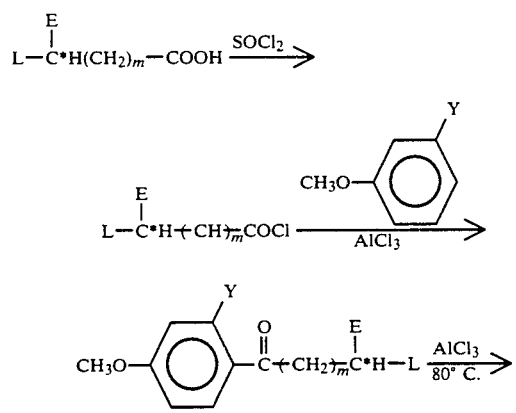

The optically active substituted phenol represented by the general formula set forth above wherein Y is hydroxyl group and k is zero may be prepared by the following process:

The substituted phenols each represented by the general formula set forth above wherein k is 1 may be prepared by the following process:

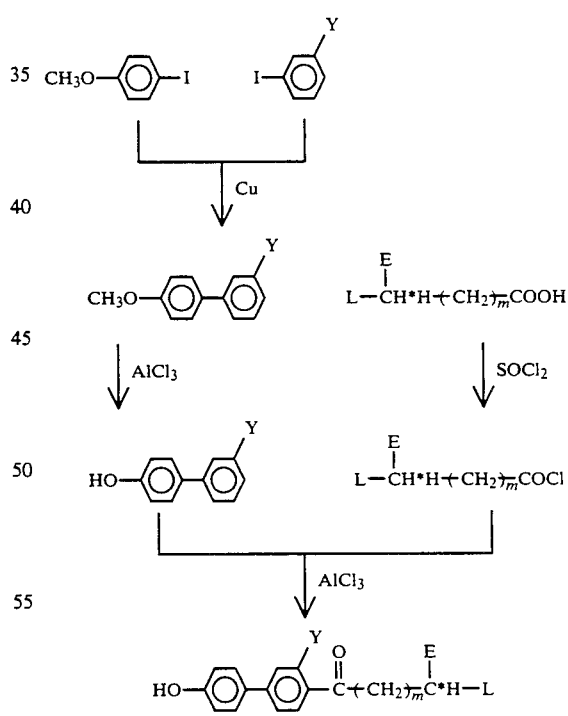

Optically active carboxylic acids usable in the reactions set forth above include those which will be listed below. In the following abridged chemical formulae, Me stands for methyl group, Et stands for ethyl group, Pr stands for propyl group, Bu stands for butyl group, Hex stands for hexyl group, Oc stands for octyl group and Ph stands for phenyl group.

Et-C*H(Me)-COOH,
Et-C*H(Me)-CH₂—COOH,
Hex-C*H(Me)COOH,
(Me)₂-CH(CH₂)₃C*H(Me)COOH,
Et-CH(Me)-C*H(Me)-(CH₂)₂—COOH,
Et-C*H(Me)-(CH₂)₂—COOH,
Ph-C*H(Me)-COOH,
Ph-C*H(Me)-CH₂—COOH,
Ph-C*H(Me)-(CH₂)₃—COOH,
Et-C*H(Me)-C*H(Cl)—COOH,
(Me)₂-CH—C*H(CF₃)—COOH,
He—C*H(Cl)—COOH,
He—C*H(CF₃)—COOH,
BuC*H(F)—(CH₂)₂—COOH,

Pr—C*H(Me)-COOH,
(Me)₂CH—C*H(Me)-COOH
Oc-C*H(Me)COOH,

Et-C*H(Me)-(CH₂)₄—COOH,
Ph-CH₂—C*H(Me)-COOH,
Ph-CH₂—C*H(Me)-CH₂—COOH,
(Me)₂-CH—C*H(Cl)—COOH,
Et-C*H(F)—COOH,
(Me)₂-CH—C*H(F)—COOH,
(Me)₂-CH—(CH₂)₃—C*H(Cl)—COOH,
Et-C*H(Cl)—CH₂—COOH,
Et-C*H(CF₃)—CH₂—COOH,

Examples and preparation examples of this invention will now be described. However, it is noted hereby that the principle and scope of this invention should not be restricted by the following examples. In the following examples, optically active carboxylic acids used as the starting materials are S-type carboxylic acids. Liquid crystal material having the same phase transition temperatures may be obtained by using R-type optically active carboxylic acids. However, the sign of optical rotation, the helical twist sense and the sign of spontaneous polarization are reversed depending on the type (S-type or R-type) of the used carboxylic acids.

EXAMPLES 1 TO 42

Compounds represented by the general formula (I) were synthesized. The phase transition temperatures and spontaneous polarizations of the synthesized compounds are shown in Table 1. The spontaneous polarization was measured at a temperature lower than the upper limit for the Sc* phase by 10° C. In Table 1, Cr indicates the crystalline phase, Sx indicates the smectic X phase, Sc* indicates the chiral smectic C phase, SA indicate the smectic A phase, N indicates the nematic phase and I indicates the isotropic liquid phase; Me stands for methyl group, Et stands for ethyl group, i-Pr stands for isopropyl group, Hex stands for n-hexyl group, Oc stands for n-octyl group; and n—C₆O stands for n—C₆H₁₃O, n—C₈O stands for n—C₈H₁₇O, n—C₉O stands for n—C₉H₁₉O, n—C₁₀O stands for n—C₁₀H₂₁O, and n—C₁₄O stands for n—C₁₄H₂₉O. Ph— stands for phenyl group, —Ph— stands for 1,4-substituted phenylene group, —Ph—Ph— stands for 4,4'-substituted diphenylene group, —Ph(F)— stands for 1,4-substituted phenyl group having fluorine at the ortho-positionto R, —Py— stands for 2,5-substituted pyrimidine group, —CH stands for 1,4-substituted cyclohexane group, n—C₈ stands for n—C₈H₁₇ and n—C₉ stands for n—C₉H₁₉.

TABLE 1

$$R-Z-COO-\phantom{}_k\phantom{}-\text{Ph}-\text{Ph}(Y)-O-\overset{O}{\underset{\|}{C}}-(CH_2)_m-\overset{E}{\underset{|}{C^*H}}-L$$

| Example No. | R | Z | k | Y | m | E | L | Cr | Sx | Sc* | SA | N | I | Ps (nC/cm²) |
|---|---|---|---|---|---|---|---|---|---|---|---|---|---|---|
| 1 | n-C₆O | —Ph—Ph— | 0 | H | 0 | Me | Et | • 130 | | • 132 | • 194 | | • | 56 |
| 2 | n-C₈O | —Ph—Ph— | 0 | H | 0 | Me | Et | • 78 | (• 65) | • 126 | • 184 | | • | 53 |
| 3 | n-C₉O | —Ph—Ph— | 0 | H | 0 | Me | Et | • 76 | (• 72) | • 129 | • 189 | | • | 52 |
| 4 | n-C₁₀O | —Ph—Ph— | 0 | H | 0 | Me | Et | • 74 | (• 63) | • 119 | • 182 | | • | 50 |
| 5 | n-C₈O | —Ph— | 0 | H | 0 | Me | Et | • 47 | | (• 10) | (• 41) | | • | |
| 6 | n-C₁₀O | —Ph— | 0 | H | 0 | Me | Et | • 52 | | | (• 45) | | • | |
| 7 | n-C₁₄O | —Ph— | 0 | H | 0 | Me | Et | • 55 | | | (• 55) | | • | |
| 8 | n-C₆O | —Ph—Ph— | 0 | OH | 0 | Me | Et | • 77 | | (• 72) | • 163 | | • | 77 |
| 9 | n-C₈O | —Ph—Ph— | 0 | OH | 0 | Me | Et | • 49 | | • 91 | • 155 | | • | 69 |
| 10 | n-C₉O | —Ph—Ph— | 0 | OH | 0 | Me | Et | • 65 | | • 102 | • 154 | | • | 57 |
| 11 | n-C₁₀O | —Ph—Ph— | 0 | OH | 0 | Me | Et | • 62 | | • 97 | • 151 | | • | |
| 12 | n-C₈O | —Ph— | 0 | OH | 0 | Me | Et | • 35 | | | (• 10) | | • | |
| 13 | n-C₁₀O | —Ph— | 0 | OH | 0 | Me | Et | • 29 | (• 0) | (• 17) | | | • | |
| 14 | n-C₁₄O | —Ph— | 0 | OH | 0 | Me | Et | • 38 | | | (• 30) | | • | |
| 15 | n-C₉ | —Ph— | 0 | OH | 0 | Me | Et | • 36 | | | | | • | |
| 16 | n-C₈O | —Ph(F)— | 0 | OH | 0 | Me | Et | • 55 | | | (• 14) | | • | |
| 17 | n-C₈O | —Ph— | 1 | H | 0 | Me | Et | • 84 | (• 78) | • 167 | | | • | |
| 18 | n-C₈O | —Ph— | 1 | OH | 0 | Me | Et | • 49 | | | • 117 | • 118 | • | |
| 19 | n-C₈O | —Ph—CH— | 0 | H | 0 | Me | Et | • 80 | | | • 163 | | • | |
| 20 | n-C₉O | —Ph—CH— | 0 | OH | 0 | Me | Et | • 46 | | | • 103 | | • | |
| 21 | n-C₈ | —Py—Ph— | 0 | H | 0 | Me | Et | • 123 | | | • 133 | | • | |
| 22 | n-C₈ | —Py—Ph— | 0 | OH | 0 | Me | Et | • 76 | | | • 103 | | • | |
| 23 | n-C₈O | —Ph—Ph— | 0 | Cl | 0 | Me | Et | • 83 | | • 111 | • 144 | | • | 29 |
| 24 | n-C₈O | —Ph—Ph— | 0 | Me | 0 | Me | Et | • 87 | | • 91 | • 125 | | • | 46 |
| 25 | n-C₈O | —Ph— | 0 | OH | 1 | Me | Et | • 31 | (• 12) | • 43 | | | • | |
| 26 | n-C₈O | —Ph—Ph— | 0 | OH | 1 | Me | Et | • 80 | | • 98 | • 170 | | • | 2.5 |
| 27 | n-C₁₀O | —Ph—Ph— | 0 | OH | 1 | Me | Et | • 60 | | • 120 | • 167 | | • | 3.9 |
| 28 | n-C₈O | —Ph—Ph— | 0 | Cl | 1 | Me | Et | • 46 | | • 124 | • 156 | | • | |
| 29 | n-C₈O | —Ph— | 0 | Cl | 1 | Me | Et | • 30 | (• 7.5) | (• 27) | | | • | |
| 30 | n-C₈O | —Ph(F)— | 0 | OH | 1 | Me | Et | • 43 | | | | | • | |
| 31 | n-C₈O | —Ph— | 0 | OH | 2 | Me | Et | • 32 | | | • 57 | | • | |
| 32 | n-C₈O | —Ph—Ph— | 0 | OH | 2 | Me | Et | • 64 | | • 127 | • 184 | | • | 6.7 |
| 33 | n-C₁₀O | —Ph—Ph— | 0 | OH | 2 | Me | Et | • 65 | | • 134 | • 177 | | • | 6.1 |

TABLE 1-continued $$R-Z-COO-\left(\bigcirc\right)_k-\underset{Y}{\bigcirc}-\underset{\|}{\overset{O}{C}}-(CH_2)_m-\underset{L}{\overset{E}{C^*H}}$$

| Example No. | R | Z | k | Y | m | E | L | Cr | Sx | Phase Transition Temperature (°C.) Sc* | SA | N | I | Ps (nC/cm²) |
|---|---|---|---|---|---|---|---|---|---|---|---|---|---|---|
| 34 | n-C₈O | —Ph—Ph— | 0 | H | 0 | Me | Hex | • 79 | | • 139 | • 153 | | • | 108 |
| 35 | n-C₈O | —Ph—Ph— | 0 | OH | 0 | Me | Hex | • 33 | | • 96 | • 132 | | • | 146 |
| 36 | n-C₉O | —Ph—Ph— | 0 | OH | 0 | Me | Hex | • 14 | • 25 | • 102 | • 134 | | • | 85 |
| 37 | n-C₉O | —Ph—Ph— | 0 | OH | 0 | Me | Oc | • 44 | | • 96 | • 124 | | • | 77 |
| 38 | n-C₈O | —Ph—Ph— | 0 | H | 0 | Cl | i-Pr | • 104 | | • 127 | • 172 | | • | |
| 39 | n-C₁₀O | —Ph— | 0 | H | 0 | Me | Ph— | • 85 | | | | | • | |
| 40 | n-C₁₀O | —Ph— | 0 | OH | 0 | Me | Ph— | • 83 | | | | | • | |
| 41 | n-C₈O | —Ph—Ph— | 0 | H | 0 | Me | Ph— | • 120 | | | | | • | |
| 42 | n-C₈O | —Ph—Ph— | 0 | OH | 0 | Me | Ph— | • 120 | | (• 81) | | | • | |

PREPARATION EXAMPLE 1 (Corresponding to Example 2)

Synthesis of 4-(1-oxo-2-methylbutyl)phenyl 4-(4'-octyloxyphenyl)benzoate (1) Synthesis of 4(1-oxo-2-methylbutyl)phenol 7.4 g (79 millimols) of phenol was dissolved in 100 ml of anhydrous methylene chloride to obtain a solution which was cooled to below 0° C. 21.0 g (158 millimols) of pulverized aluminium trichloride was added to the solution little by little. A solution prepared by dissolving 9.48 g (79 millimols) of S-(+)-2-methylbutanoic acid chloride in 50 ml of anhydrous methylene chloride was dropwisely added over a period of an hour under stirring. After the completion of dropwise addition, the reaction mixture was refluxed for 4 hours. The reaction mixture was then cooled to the room temperature and added slowly to 200 g of crushed ice. Additional 100 ml of methylene chloride was added, and the organic phase having an orange yellow color was separated from the aqueous phase. The separated solution in methylene chloride was subjected to extraction for two times using a 5% aqueous solution of NaOH to extract the product. The extracts were joined together and dilute hydrochloric acid was added thereto to adjust the pH value of the joined extraxt to pH 5. The product was extracted with 100 ml of ethyl ether for two times. The extract in ethyl ether was rinsed with water and dried over anhydrous sodium sulfate. The solvent was distilled off from the extract to obtain 2.1 g of a viscous liquid product. The liquid product was refined through silica gel column chromatography (using Wako Gel C-200 available from Wako Junyaku K.K., and using chroloform as the eluent) to obtain 1.3 g of liquid 4-(1-oxo-2-methylbutyl)-phenol.

The product was identified by the infra-red absorption spectrum and by the proton NMR ($^1$HMNR).

IR Spectrum (cm$^{-1}$): 3305, 1651, 1602, 1578, 1221.

$^1$HNMR, δ ppm (CDCl₃): 0.91 (—CH₂CH₃), 1.18 (—C*H—CH₃), 1.49 and 1.82 (—C*H—CH₂CH₃), 3.36 (—CH—), 6.03 (OH), 6.90 (Hydrogen of benzene ring at the ortho-position to OH), 7.92 (Hydrogen of benzene ring at the ortho-position to CO).

(2) Synthesis of 4-(1-oxo-2-methylbutyl)phenyl 4-(4'-octyloxyphenyl)benzoate 250 mg of 4-(1-oxo-2-methylbutyl)phenol was dissolved in 15 ml of anhydrous pyridine, and then a solution prepared by dissolving 700 mg of 4-(4'-octyloxyphenyl)benzoic acid chloride in 20 ml of anhydrous methylene chloride was added dropwisely over a period of about an hour under stirring. The reaction mixture was stirred at the room temperature for additional 40 hours, and then added to 300 ml of dilute hydrochloric acid solution. 50 ml of chloroform and 50 ml of ethyl ether were added, followed by sufficient shaking, and then the organic phase was separated from the aqueous phase. The organic phase was rinsed with a dilute hydrochloric acid solution for two times, rinsed with an aqueous solution of NaHCO₃ for one time, and further rinsed with a 3% aqueous solution of NaCl for three times. The rinsed organic phase was dried by adding anhydrous Na₂SO₄. After removing the drying agent by filtration, the solvent was distilled off to obtain 200 mg of a reaction product. The reaction product was refined through silica gel column chromatography while using chloroform as the eluent. The thus obtained product was recrystallized from a mixed solvent composed of 10 parts by volume of ethyl acetate and 90 parts by volume of n-hexane. 75 mg of 4-(1-oxo-2-methylbutyl)phenyl 4-(4'-octyloxyphenyl)benzoate was obtained.

IR (KBr) (cm$^{-1}$): 2926, 1737, 1678, 1602, 828, 766.

$^1$HNMR δ ppm (CDCl₃): 0.90, 0.94, 1.22, 1.30 to 1.36, 1.46 to 1.51, 1.69 to 1.78, 3.41, 4.02, 7.01, 7.35, 7.60, 7.70, 8.06, 8.23.

PREPARATION EXAMPLE 2 (Corresponding to Example 9)

Synthesis of 3-hydroxy-4-(1-oxo-2-methylbutyl)phenyl 4-(4'-octyloxyphenyl)benzoate (1) Synthesis of 3-hydroxy-4-(1-oxo-2-methylbutyl)phenol 16.3 g of anhydrous zinc chloride was dissolved in 10.3 g of S-(+)-2-methylbutanoic acid by heating to 110° C. 13.2 g of resorcinol was added to the mixture and then the temperature of the admixture was raised to 150° C. over a period of 30 minutes under stirring. The reaction mixture was then cooled to the room temperature, and a mixture composed of 25 ml of hydrochloric acid and 25 ml of water was added thereto. The reaction mixture was then subjected to extraction for three times, each by using 50 ml of ethyl ether. The extracts were joined together and rinsed with an aqueous solution of NaHCO₃ for three times, and then rinsed with water for three times. Anhydrous Na₂SO₄ was added to the rinsed extract to dry the ethyl ether extract. Ethyl ether was removed to obtain a liquid reaction product which was refined through silica gel column chromatography while using chloroform as the eluent. As a result, 6.2 g of 3-hydroxy-4-(1-oxo-2-methylbutyl)-phenol was obtained.

IR (cm$^{-1}$): 3361, 1629, 1601, 1514, 1443, 1383, 1231, 1132.

$^1$HNMR δ ppm (CDCl$_3$): 0.93 (—CH$_2$CH$_3$), 1.20 (—C*H—CH$_3$), 1.51 and 1.83 (—C*H—CH$_2$CH$_3$), 3.33 (—C*H—), 5.67 (Hydrogen of OH at the paraposition to carbonyl), 6.39 (Hydrogen sandwitched by two OH groups), 6.93 (Hydrogen at the meta-position to carbonyl).

(2) Synthesis of
3-hydroxy-4-(1-oxo-2-methylbutyl)phenyl
4-(4'-octyloxyphenyl)benzoate 0.5 g of 3-hydroxy-4-(1-oxo-2-methylbutyl)phenol prepared by the process described in (1) was dissolved in 15 ml of anhydrous pyridine, to which added was a solution of 0.7 g of 4-(4'-octyloxyphenyl)benzoic acid chloride dissolved in 20 ml of anhydrous methylene chloride dropwisely over a period of about one hour under stirring. The reaction mixture was stirred at the room temperature for additional 40 hours to proceed the reaction. Then, the reaction mixture was added to 300 ml of dilute hydrochloric acid solution. After adding 50 ml of chloroform and 50 ml of ethyl ether, followed by shaking, the organic phase was separated from the aqueous phase. The organic phase was rinsed with a dilute hydrochloric acid solution for two times, rinsed with an aqueous solution of NaHCO$_3$ for one time, and then rinsed with a 3% aqueous solution of NaCl for three times. Anhydrous Na$_2$SO$_4$ was added to the organic phase to dry the same. After removing the drying agent by filtration, the solvent was distilled off to obtain a crude product which was refined through silica gel column chromatography while using chloroform as the eluent. The thus obtained product was recrystallized from a mixed solvent composed of 10 parts by volume of chloroform and 90 parts by volume of n-hexane. As a result, 0.08 g of 3-hydroxy-4-(1-oxo-2-methylbutyl)phenyl 4-(4'-octyloxyphenyl)benzoate was obtained.

IR (KBr) (cm$^{-1}$): 2929, 1736, 1638, 1605, 1256, 828, 766.

$^1$HNMR δ ppm (CDCl$_3$): 0.90, 0.95, 1.24, 1.30 to 1.34, 1.39 to 1.60, 1.78 to 1.84, 3.41, 4.02, 6.83, 6.89, 7.00, 7.59, 7.70, 7.86, 8.21.

PREPARATION EXAMPLE 3 (Corresponding to Example 16)

Synthesis of 3-hydroxy-4-(1-oxo-2-methylbutyl)phenyl (S)-3-fluoro-4-octyloxybenzoate 0.7 g of 3-fluoro-4-octyloxybenzoic acid chloride and 0.5 g of (S)-hydroxy-4-(1-oxo-2-methylbutyl)phenol were subjected to a process similar to that described in Preparation Example 1, whereby 1.32 g of a crude product of (S)-3-hydroxy-4-(1-oxo-2-methylbutyl)phenyl 3-fluoro-4-octyloxybenzoate was obtained. The resultant crude product was recrystallized from ethanol added with pyridine. Then, the crystalline product was refined through silica gel column chromatography while using chloroform as the eluent. The refined crystal was further recrystallized for two times from ethanol to obtain 380 mg of a white crystal. The purity of the white crystal was determined by liquid chromatography while using O.D.S (octadecylsiloxane) as the stationary phase and using tetrahydrofuran/methanol as the eluent. The result was that the purity of the white crystal was 100%.

IR (cm$^{-1}$): 2928, 2856, 1736, 1638, 1616, 1284, 1126 754.

$^1$HNMR δ ppm (CDCl$_3$): 0.89 (3H, t, —CH$_3$), 0.95 (3H, t —CH$_3$), 1.23 (3H, d, CH—CH$_3$), 1.25 to 1.5 (11H m, (CH$_2$)$_{10}$ and CH—CH—CH$_3$), 1.87 (3H, m, —CH$_2$—CH$_2$—O—Ph and CH—CH—CH$_3$), 3.40 (1H, m —CH—), 4.12 (2H, t, —CH$_2$—O—Ph), 6.79 (1H, d para to OH), 6.86 (1H, d, ortho to OH), 7.03 (1H, d meta to F), 7.85 (1H, d, meta to OH), 7.88 (1H, d, ortho to F), 7.94 (1H, d, para to F).

PREPARATION EXAMPLE 4 (Corresponding to Example 17)

Synthesis of (S)-4-(1-oxo-2-methylbutyl)-4-diphenyl 4-octyloxybenzoate (1) Synthesis of
(S)-4-hydroxy-4'-(1-oxo-2-methylbutyl)-diphenyl 34 g (0.2 mol) of 4-hydroxydiphenyl was dissolved in a solution composed of 20 g (0.36 mol) of KOH, 200 ml of water and 400 ml of methanol. 28.4 g (0.2 mol) of CH$_3$I (methyl iodide) was added to the reaction solution. The reaction mixture was refluxed for 4 hours, and then cooled. The cooled reaction mixture was added to 1000 ml of water, whereby a white precipitate was formed. The precipitate was filtered, rinsed with water and then recrystallized from ethanol. 26.5 g (0.144 mol) of 4-methoxydiphenyl was obtained.

6.0 g (32.6 millimols) of 4-methoxydiphenyl was dissolved in 100 ml of anhydrous methylene chloride to obtain a solution which was cooled below 0° C. 4.35 g (32.6 millimols) of pulverized AlCl$_3$ was added to the cooled solution little by little. A solution prepared by dissolving 4.0 g (33.2 millimols) of (S)-(+)-2-methylbutanoic acid chloride in 50 ml of anhydrous methylene chloride was dropwisely added to the mixture over a period of about an hour. After the completion of dropwise addition, the reaction mixture was stirred at the room temperature for 3 hours. The reaction mixture was then added to 500 g of crushed ice. 100 ml of methylene chloride was added to the reaction mixture, and then the organic phase was separated from the aqueous phase. The separated organic phase was rinsed with an aqueous solution of NaHCO$_3$ and water, and dried by adding anhydrous Na$_2$SO$_4$. After removing the drying agent by filtration, the solvent was distilled off to obtain 3.65 g of a crude product. The crude product was refined through silica gel column chromatography while using a mixed solvent composed of 50 parts by volume of chloroform and 50 parts by volume of hexane as the eluent. 1.15 g of (S)-4-methoxy-4'-(1-oxo-2-methylbutyl)diphenyl was obtained.

IR (cm$^{-1}$): 1680, 828, 770.

$^1$HNMR δ ppm (CDCl$_3$): 0.94 (3H, t, —CH$_2$CH$_3$) 1.21 (3H, d, —C*H—CH$_3$), 1.52 and 1.86 (2H, m, —C*H—CH$_2$—CH$_3$), 3.41 (1H, m, C*H), 3.86 (3H, s OCH$_3$), 7.00 (2H, d), 7.57 (2H, d), 7.64 (2H, d), 8.00 (2H d).

0.5 g (1.86 millimols) of (S)-4-methoxy-4'-(1-oxo-2 methylbutyl)diphenyl was dissolved in 30 ml of anhydrous 1,2-dichloroethane to obtain a solution. 0.49 g (3.67 millimols) of pulverized AlCl$_3$ was added to the solution and the solution was subjected to reflux for 30 minutes. The reaction mixture was cooled to the room temperature and added to 200 g of crushed ice. After adding 100 ml of chroloform, the organic phase was separated from the aqueous phase. The separated organic phase was rinsed with water and then dried by adding anhydrous Na$_2$SO$_4$. After removing the drying agent by filtration, the solvent was distilled off to obtain 0.29 g of a crude product which was refined through silica gel column chromatography while using chloroform as the eluent. 0.17 g of (S)-4-hydroxy-4'-(1-oxo-2-methylbutyl)diphenyl was obtained.

(2) Synthesis of (S)-4'-(1-oxo-2-methylbutyl)-4-diphenyl 4-octyloxybenzoate

Generally following to the procedure as described in Preparation Example 1, (S)-4-hydroxy-4'-(1-oxo-2-methylbutyl)diphenyl and (S)-4-octyloxybenzoic acid chloride were reacted to prepare (S)-4-(1-oxo-2-methylbutyl)-4-diphenyl 4-octyloxybenzoate.

Specific Rotation $[\alpha]_D^{25}$: +10.2° (C=2.0, CHCl$_3$).
IR (KBr) (cm$^{-1}$): 1715, 1668, 1598.
$^1$HNMR δ ppm (CDCl$_3$): 0.87 to 0.98 (6H, m, 2C$\underline{H_2}$C$\underline{H_3}$), 1.23 (3H, d, C*H—C$\underline{H_3}$), 1.30 to 1.87 (14H, m, C$\underline{H_2}$), 3.44 (1H, m, C*H), 4.05 (2H, t, CH$_2$O), 6.99 (2H, d, arom H), 7.31 (2H, d arom H), 7.68 (4H, d+d, arom H), 8.05 (2H, d, arom H), 8.16 (2H, d, arom H).

PREPARATION EXAMPLE 5 (Corresponding to Example 18)

Synthesis of (S)-3-hydroxy-4'-(1-oxo-2-methylbutyl)-4-diphenyl 4-octyloxybenzoate (1) Synthesis of 3,4'-dimethoxy-1,1'-diphenyl 70.2 g (0.3 mol) of m-iodoanisole and 70.2 g (0.3 mol) of p-iodoanisole were heated to 60°±5° C. 165 g of a copper powder was added to allow the mixture to react at a temperature of 200° to 220° C. for 12 hours. 450 ml of toluene was added to the reaction mixture to dissolve the reaction product. The insoluble substances were filtered off, and toluene serving as the solvent was distilled off to obtain a crude crystal. The crude crystal was purified through column chromatography while using a mixed solvent composed of 20 parts by volume of n-hexane and 1 part by volume of ethyl acetate as the eluent. The product was recrystallized from ethanol. 17.4 g of 3,4'-dimethoxy-1,1'-diphenyl was obtained in the form of a white crystal (Yield: 27%) having a melting point of 59.5° to 61.0° C.

(2) Synthesis of 3,4'-dihydroxy-1,1'-diphenyl 15.9 g (0.075 mol) of 3,4'-dimethoxy-1,1'-diphenyl and 45 g of AlCl$_3$ were added to 225 ml of toluene, and refluxed for 8 hours under stirring. The reaction solution was added to a dilute hydrochloric acid solution, and the reaction product was extracted by using ethyl acetate. The organic phase was separated, rinsed with water, and then dried by adding anhydrous Na$_2$SO$_4$. The drying agent was removed by filtration and the solvent was distilled off to obtain a brown oily product. The brown oily product was refined through column chromatography while using n-hexane as the eluent. The refined product was recrystallized from water. 7.2 g (Yield: 52%) of 3,4'-dihyroxy-1,1'-diphenyl was obtained in the form of a white crystal having a melting point of 193° to 194.5° C.

$^1$HNMR δ ppm (CDCl$_3$): 6.78 (1H, d, 4-H), 6.93 (2H, d, 3'-H and 5'-H), 7.06 (2H, d, 2-H and 6-H), 7.23 (1H, d, 5-H), 7.41 (2H, d, 2'-H and 6'-H), 7.91 (1H, s, OH), 8.01 (1H, s, OH).

(3) Synthesis of (S)-3,4'-dihydroxy-4-(1-oxo-2-methylbutyl)-1,1'-diphenyl

A mixture composed of 6.8 g (35 millimols) of 3,4'-dihydroxy-1,1'-diphenyl, 15 ml of nitrobenzene and 5.7 g of AlCl$_3$ was heated, and 4.8 g (140 millimols) of 2-methylbutanoic acid chloride was added to the mixture. The admixture was allowed to react at a temperature of 130° to 135° C. for 4 hours under stirring. After cooling, the reaction mixture was added to a dilute hydrochloric acid solution and subjected to extraction by using ethyl acetate. The organic phase was separated and rinsed with water, and then dried by adding anhydrous Na$_2$SO$_4$. The solvent was distilled off to obtain a brown oily product which was refined through silica gel column chromatography while using a mixed solvent composed of 10 parts by volume of n-hexane and 1 part of acetone as the eluent. As a result, 2.0 g (Yield: 22%) of S-(+)-3,4'-dihydroxy-4-(1-oxo-2-methylbutyl)-1,1'-diphenyl was obtained in the form of a light yellow oily substance.

IR (Neat) cm$^{-1}$: 3350, 2960, 1610.
$^1$HNMR δ ppm (CDCl$_3$): 0.96 (3H, t, CH$_2$C$\underline{H_3}$), 1.25 (3H, d, CH—C$\underline{H_3}$), 1.50 to 1.93 (2H, m, —CHC$\underline{H_2}$CH$_3$), 3.46 (1H, m, CH), 5.34 (1H, s, 4'—OH), 6.90 (2H, d, H adjacent to OH on the benzene ring without acyl group), 7.11 (1H, d, para-H of OH on the benzene ring with acyl group), 7.18 (1H, d, ortho-H to OH on the benzene ring with acyl group) 7.53 (2H, d, meta-H to H on the benzene ring without acyl group), 7.82 (1H, d, acyl group), 12.70 (1H, s, OH at the ortho position to acyl group).

Result of Elementary Analysis: Cald.: C, 75.53%, H, 6.71%. Found: C, 75.50%; H, 6.81%.

(4) Synthesis of (S)-3'-hydroxy-4'-(1-oxo-2-methylbutyl)-4-diphenyl 4-octyloxybenzoate Generally following to the procedure as described in Preparation Example 1, 4-octyloxybenzoic acid chloride and (S)-3,4'-dihydroxy-4-(1-oxo-2-methylbutyl)-1,1'-diphenyl were reacted to obtain 3'-hydroxy-4'-(1-oxo-2-methylbutyl)-4-diphenyl 4-octyloxybenzoate.

Specific Rotation 25: +12.7° (C=2.0, CHCl$_3$).
IR (KBr) (cm$^{-1}$): 1720 (COO), 1634 (C=O), 1608.
$^1$HNMR δ ppm (CDCl$_3$): 0.87 to 0.99 (6H, m, 2CH$_3$), 1.25 (3H, d, C*H—C$\underline{H_3}$), 1.30 to 1.71 (14H, m, CH$_2$), 3.46 (1H, m, C*H), 4.05 (2H, t, CH$_2$O), 6.99 (2H, d, H adjacent to octyloxy group), 7.14 (1H, d, para-H to OH), 7.22 (1H, s, ortho-H to OH), 7.31 (2H, d, ortho-H to OCO), 7.68 (2H, d, meta-H to OCO), 7.85 (1H, d, ortho-H to acyl group), 8.16 (2H, d, ortho-H to COO).

PREPARATION EXAMPLE 6 (Corresponding to Example 20

Synthesis of 4-(1-oxo-2-methylbutyl)-3-hydroxyphenyl trans-4-(4'-nonyloxyphenyl)cyclohexyl-carboxylate Into a 1000 ml volume three-neck flask charged were 150 ml of iso-amyl alcohol and 2.06 g of 4-nonyloxyphenyl benzoic acid, followed by heating under stirring, to dissolve the latter in the former. Under reflux, a solution of 8 g of metallic sodium in 70 ml of iso-amyl alcohol prepared by heating was added to the flask. The reaction was continued for an additional 20 minutes under reflux, and then additional 8 g of metallic sodium was added to the flask. After the lapse of 30 minutes, a solution prepared by dissolving 12 g of metallic sodium in 60 ml of iso-amyl alcohol was added to the flask, and after the lapse of 40 minutes 25 ml of iso-amyl alcohol was added to the flask. The reaction mixture was further refluxed for an hour, and then cooled to the room temperature. 500 ml of water was added to the cooled reaction mixture, and then the reaction mixture was allowed to stand for one night. The reaction mixture was subjected to extraction using 200 ml of chloroform to obtain 0.9 g of trans-4-(4-nonyloxyphenyl)cyclohexylcarboxylic acid.

0.6 g of the thus obtained trans-4-(4-nonyloxyphenyl)cyclohexylcarboxylic acid was heated in toluene with 5 ml of thionyl chloride. Then, toluene was distilled off to obtain trans-4-(4-nonyloxyphenyl)cyclohexylcarboxylic acid chloride. The thus obtained acid chloride was dissolved in 40 ml of carbon tetrachloride to obtain a solution, to which added were 5 ml of pyridine and a solution prepared by dissolving 0.56 g of (S)-3-hydroxy-4-(1-oxo-2-methylbutyl)phenol in 10 ml of carbon tetrachloride. The admixture was stirred at the room temperature for a day to proceed the reaction. After refluxing for additional one hour, water was added to the admixture, and the organic phase was separated. The separated organic phase was rinsed initially with a dilute hydrochloric solution, then with an aqueous solution of $NaHCO_3$, and finally with a saturated aqueous solution of NaCl. The rinsed organic phase was dried over anhydrous $Na_2SO_4$ by allowing the same to stand for one night. The solvent was distilled off from the dried organic phase to obtain crude (S)-4-(1-oxo-2-methylbutyl)-3-hydroxyphenyl trans-4-(4-nonyloxyphenyl)cyclohexylcarboxylate. The thus obtained crude product was recrystallized from ethanol for two times to obtain 0.04 g of a recrystallized product which was identified by infra-red absorption spectrum (IR) and nuclear magnetic resonance spectrum (NMR).

IR Spectrum ($cm^{-1}$): 2924, 1760 (COO), 1638 (C=O), 1620, 1510.

$^1$HNMR δ ppm ($CDCl_3$): 0.88 (3H, t, $CH_3$), 0.93 (3H, t, $CH_3$), 1.21 (3H, d, $CHCH_3$), 1.28 (12H, m, $(CH_2)_6$), 1.4 to 1.5 (3H, m, 1H of CH—$CH_2$—$CH_3$ and equatorial $CH_2$), 1.6 to 1.9 (5H, m, $CH_2$—$CH_2$—Ph, axial $CH_2$ and 1H of CH—$CH_2$—$CH_3$), 2.02 (2H, m, equatorial $CH_2$), 2.25 (2H, m, axial $CH_2$), 2.5 to 2.6 (4H, m, axial CH), 3.37 (1H, q, —CH—), 3.93 (2H, t, $CH_2$—Ph), 6.66 (1H, dd, para to OH), 6.73 (1H, d, ortho to OH), 6.84 (2H, d, ortho to alkoxy), 7.12 (2H, d, meta to alkoxy), 7.79 (1H, d, meta to OH) 12.78 (1H, s, OH).

PREPARATION EXAMPLE 7 (Corresponding to Example 21)

Synthesis of (S)-4-(1-oxo-2-methylbutyl)phenyl 4-(5-octyl-2-pyrimidinyl)benzoate 10 ml of $CCl_4$, 5 ml of thionyl chloride and one drop of dimethylformamide were added to 2.0 g of 4-(5-octyl-2-pyrimidinyl)benzoic acid. The mixture was refluxed for 3 hours under stirring. The solvent was distilled off initially under normal pressure and then under reduced pressure. As a result, 2.2 g of 4-(5-octyl-2-pyrimidinyl)benzoic acid chloride was obtained in the form of a colorless plate-form crystal. 1.2 g of the thus obtained 4-(5-octyl-2-pyrimidinyl)benzoic acid chloride was dissolved in a mixed solvent composed of 20 ml of $CCl_4$ and 5 ml of anhydrous pyridine under stirring. The thus obtained solution was added with a solution prepared by dissolving 0.7 g of (S)-4-(1-oxo-2-methylbutyl)phenol in 10 ml of $CCl_4$, and the admixture was stirred at the room temperature for one night. The admixture was heated to reflux for 3 hours. 200 ml of water and 100 ml of ethyl ether were added to the reaction admixture, followed by stirring. The organic phase was separated, and rinsed initially with a dilute hydrochloric acid solution, then with an aqueous solution of $NaHCO_3$ and finally with a saturated aqueous solution of NaCl. The rinsed organic phase was added with anhydrous $Na_2SO_4$ and allowed to stand for one night to dry the same. After removing the drying agent by filtration, the solvent was distilled off to obtain 1.86 g of a crude product. The crude product was refined through silica gel column chromatography while using a mixed solvent of hexane/ethyl acetate (ratio by volume: 8/2). The refined product was recrystallized from ethanol to obtain 200 mg of (S)-4-(1-oxo-2-methylbutyl)phenyl 4-(5-octyl-2-pyrimidinyl)benzoate in the form of a colorless crystal.

IR Spectrum ($cm^{-1}$): 2940, 1740 (COO), 1680 (C=O).

$^1$HNMR δ ppm ($CDCl_3$): 0.88 (3H, t, $CH_3$), 0.94 (3H, t, $CH_3$), 1.16 (3H, d, CH—$CH_3$), 1.2 to 1.4 (10H, m, $(CH_2)_5$), 1.52 and 1.86 (2H, m, —CH—$CH_2$—$CH_3$), 1.68 (2H, m, —$CH_2$—$CH_2$-pyrimidine), 2.66 (2H, t, —$CH_2$-pyrimidine), 3.40 (1H, q, —CH—), 7.36 (2H, d, meta to CO), 8.05 (2H, d, ortho to CO), 8.30 (2H, d, meta to COO), 8.58 (2H, d, ortho to COO), 8.68 (2H, s, pyrimidine-H).

m/e: 472 (M+), 296.

PREPARATION EXAMPLE 8 (Corresponding to Example 23

(1) Synthesis of 2-chloro-4-(1-oxo-2-methylbutyl)phenol 11.3 g (79 millimols) of m-chloroanisole was dissolved in 100 ml of anhydrous 1,2-dichloroethane to obtain a solution which was cooled below 0° C. 10.5 g of pulverized $AlCl_3$ (79 millimols) was added to the cooled solution little by little. The thus obtained mixture was added dropwisely with a solution prepared by dissolving 9.48 g (79 millimols) of S-(+)-2-methylbutanoic acid chloride in 50 ml of 1,2-dichloroethane over a period of an hour under stirring. After the completion of dropwise addition, the reaction mixture was further added with 10.5 g of pulverized $AlCl_3$, followed by reflux for 4 hours. Then, the reaction mixture was cooled to the room temperature and added to 500 g of crushed ice little by little. 200 ml of chloroform was then added to the reaction mixture. The organic phase was separated from the reaction mixture and rinsed with water. Anhydrous $Na_2SO_4$ was added to the rinsed organic phase to dry the same. The drying agent was removed by filtration, and the solvent was removed by distillation to obtain 5.5 g of a viscous liquid product. The thus obtained viscous liquid product was refined through silica gel column chromatography while using chloroform as the eluent. As a result, 2.3 g of 2-chloro-4-(1-oxo-2-methylbutyl)phenol in the form of a liquid.

IR Spectrum ($cm^{-1}$): 3340, 2980, 1670, 1597, 1569, 1295, 1221, 1053, 903.

$^1$HNMR δ ppm ($CDCl_3$): 0.92, 1.17, 1.45, 1.79, 3.26, 5.88, 6.77, 6.90, 7.37.

(2) Synthesis of 2-chloro-4-(1-oxo-2-methylbutyl)phenyl 4-(4'-octyloxyphenyl)benzoate 450 g of 2-chloro-4-(1-oxo-2-methylbutyl)phenol was dissolved in 15 ml of anhydrous pyridine. A solution prepared by dissolving 700 mg of 4-(4'-octyloxyphenyl)benzoic acid chloride in 20 ml of anhydrous methylene chloride was then added dropwisely over a period of an hour under stirring. The reaction mixture was stirred at the room temperature for 40 hours, and then maintained in the boiling condition for 3 hours. Thereafter, the reaction mixture was cooled to the room temperature, and the cooled reaction mixture was added to 300 ml of a dilute hydrochloric acid solution. 50 ml of chloroform and 50 ml of ethyl ether were added, followed by sufficient shaking, and then the organic phase was separated. The separated organic phase was rinsed with a dilute hydrochloric acid solution for two times, then with an aqueous solution of $NaHCO_3$ for one time, and finally with a 3% aqueous solution of NaCl for three times. The organic phase was dried by adding anhydrous $Na_2SO_4$. The drying agent was removed by filtration and the organic solvent was removed by distillation to obtain 900 mg of a reaction product which was refined through silica gel column chromatography while using chloroform as the eluent. The refined product was recrystallized from ethanol to obtain 242 mg of 2-chloro-4-(1-oxo-2-methylbutyl)phenyl 4-(4'-octylphenyl)benzoate.

IR Spectrum (KBr, $cm^{-1}$): 2957, 1740, 1695, 1603, 1263, 1197, 1068, 830, 766.

$^1$HNMR δ ppm ($CDCl_3$): 0.90, 0.93, 1.21, 1.28, 4.02, 7.03, 7.24, 7.35, 7.38, 7.59, 7.72, 8.22.

PREPARATION EXAMPLE 9 (Corresponding to Example 24)

Synthesis of 3-methyl-4-(1-oxo-2-methylbutyl)phenyl 4-(4'-octyloxyphenyl)benzoate (1) Syntesis of 3-methyl-4-(1-oxo-2-methylbutyl phenol Generally following to the procedure as described in paragraph (1) of Preparation Example 1, m-cresol and (S)-(+)-2-methylbutanoic acid chloride were reacted to obtain 3-methyl-4-(1-oxo-2-methylbutyl)phenol.

IR Spectrum ($cm^{-1}$): 3350, 1658, 1605, 1576, 1220.

$^1$HNMR δ ppm ($CDCl_3$): 0.90 (3H, t, $CH_3\underline{CH_3}$), 1.14 (3H, d, $CH\underline{CH_3}$), 1.43 and 1.79 (2H, m, $CH\underline{CH_2}CH_3$), 2.46 (3H, s, $\underline{Ph}-CH_3$), 5.13 (1H, s, OH), 6.70 (2H, m, ortho-H to OH), 7.57 (1H, d, ortho-H to CO).

(2) Synthesis of 3-methyl-4-(1-oxo-2-methylbutyl)phenyl 4-(4'-octyloxyphenyl)benzoate Generally following to the procedure as described in paragraph (2) of Preparation Example 1, 3-methyl-4-(1-oxo-2-methylbutyl)phenol was reacted with 4-(4'-octyloxyphenyl)benzoic acid chloride to obtain 3-methyl-4-(1-oxo-2-methylbutyl)phenyl 4-(4'-octyloxyphenyl)benzoate.

IR Spectrum ($cm^{-1}$): 2929, 1740, 1686, 1608, 1277, 1080, 835, 765.

$^1$HNMR δ ppm ($CDCl_3$): 0.90, 0.93, 1.15, 1.26 to 1.55, 1.78, 2.45, 3.22, 4.05, 6.97, 7.31, 7.60, 7.70, 8.03, 8.14.

PREPARATION EXAMPLE 10 (Corresponding to Example 38)

Generally following to the procedures as described in Preparation Example 1, 4-(1-oxo-2-chloro-3-methylbutyl)phenyl 4-(4'-octyloxyphenyl)benzoate was prepared from (S)-(−)-2-chloro-3-methylbutanoic acid chloride.

IR Spectrum ($cm^{-1}$): 1738, 1695, 1604, 1078, 838, 770.

$^1$HNMR δ ppm ($CDCl_3$): 0.90 (3H, t, $CH_2\underline{CH_3}$), 1.04 (3H, d, $CH\underline{CH_3}$), 1.14 (3H, d, $CH\underline{CH_3}$), 1.25 to 1.6 (10H, m, $CH_2$), 1.82 (2H, m, $OCH_2\underline{CH_2}$), 2.51 (1H, m, $CH\underline{CH_3}$), 4.02 (2H, t, $OCH_2$), 4.91 (1H, d, $C\underline{H}Cl$), 7.01 (2$\underline{H}$, d), 7.38 (2H, d), 7.60 (2H, d), 7.70 (2H, d), 8.09 (2H, d), 8.23 (2H, d).

PREPARATION EXAMPLE 11 (Corresponding to Example 40)

3.0 g (20 millimols) of S-(+)-2-phenylpropionic acid was mixed with 3.3 g (24 millimols) of anhydrous zinc chloride and heated to 110° C. to dissolve the latter in the former. 2.64 g (24 millimols) of resorcinol was added to the solution and further heated to 150° C. over a period of 20 minutes while stirring the reaction mixture. The reaction mixture was then cooled to the room temperature. 10 ml of concentrated hydrochloric acid solution and 50 ml of water was added to the reaction mixture, and the reaction product was extracted for 3 times while using 50 ml of ethyl ether in each extraction operation. The extract in ethyl ether was rinsed with an aqueous solution of $NaHCO_3$ for two times, and then rinsed with water for three times. The extract in ethyl ether was then dried by adding anhydrous $Na_2SO_4$. The drying agent was removed by filtration and ethyl ether was removed by distillation to obtain 3.6 g of a crude product. The crude product was refined through silica gel column chromatography while using chloroform as the eluent. As a result, 2.0 g of 3-hydroxy-4-(1-oxo-2-phenylpropyl)phenol was obtained.

IR Spectrum ($cm^{-1}$): 3352, 1628, 1452, 1376, 1230, 1170, 825.

600 mg (2.5 millimols) of the thus obtained 3-hydroxy-4-(1-oxo-2-phenylpropyl)phenol was reacted with 830 mg (2.4 millimols) of 4-(4'-octyloxyphenyl)benzoic acid chloride, similar to the procedure as described in Preparation Example 2, to obtain 960 mg of a crude product. The crude product was refined through silica gel column chromatography while using a mixed solvent of chloroform/hexane (50/50) as the eluent. The refined product was recrystallized from a mixed solvent of chloroform/ethanol (20/80) to obtain 153 mg of 3-hydroxy-4-(1-oxo-2-phenylpropyl)phenyl 4-(4'-octylphenyl)benzoate.

IR ($cm^{-1}$): 2924, 1738, 1634, 1606, 1498, 1248, 1132, 1066, 824, 764.

EXAMPLE 43

A liquid crystal composition was prepared by using the compound of Example 11 which is one of the liquid crystal compounds represented by the general formula (I) together with the following liquid crystal compound (A).

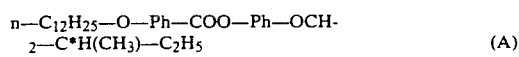    (A)

The liquid crystal composition was prepared by weighing the liquid crystal compounds which were mixed together and then heated to form a fused mass. The phase diagram of the thus prepared liquid crystal composition is shown in FIG. 1. It will be seen from FIG. 1 that a ferroelectric liquid crystal composition exhibiting the Sc* phase in a wide temperature range including the room temperature can be prepared by adding the compound (A).

EXAMPLE 44

A liquid crystal composition was prepared by using the compound of Example 11 together with the following liquid crystal compound (B).

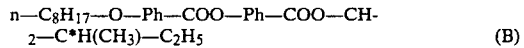

The phase diagram of the thus prepared liquid crystal composition is shown in FIG. 2. It will be seen from FIG. 2 that a ferroelectric liquid crystal composition exhibiting the Sc* phase in a wide temperature range including the room temperature can be prepared by adding the compound (B).

EXAMPLE 45

A liquid crystal composition was prepared by mixing the compounds of Examples 11 and 12. The phase diagram of the thus prepared liquid crystal composition is shown in FIG. 3. A ferroelectric liquid crystal composition containing 80 wt % of the compound of Example 11 exhibited the Sc* phase within a temperature range of from 50° to 20° C.

EXAMPLE 46

The compound of Example 9 and the liquid crystal compound (B) set forth above were mixed in an equal ratio by weight to prepare a liquid crystal composition. The phase transition temperatures of the liquid crystal composition were as follows: Cr 23 Sc* 49 SA 96° C. I

EXAMPLE 47

The compound of Example 11 and a liquid crystal compound (C) set forth below were mixed in an equal ratio by weight to prepare a liquid crystal composition.

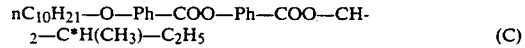

The phase transition temperatures of the liquid crystal composition were as follows: Cr 3 Sc* 58 SA 96° C. I

EXAMPLE 48

The compound of Example 9 and liquid crystal compounds as set forth below were mixed together to prepare a liquid crystal composition.

| | |
|---|---|
| n-C8H17O-Ph-Ph-COO-Ph(OH)—CO—C*H(CH3)—C2H5 | 25 wt % |
| n-C8H17O-Ph-COO-Ph-COO—CH2—C*H(CH3)—C2H5 | 25 wt % |
| n-C8H17O-Ph-COO-Ph-Ph-O—CH2—C*H(CH3)—C2H5 | 50 wt % |

The phase transition temperatures of the liquid crystal composition were Cr 14 Sc* 39 SA 117 Ch 120° C. I. The liquid crystal composition had a cholesteric phase (Ch), and exhibited the Sc* phase within a wide temperature range including the room temperature.

EXAMPLE 49

A liquid crystal element is fabricated and subjected to test by using a liquid crystal composition composed of 67 wt % of the liquid crystal compound of Example 11 and 33 wt % of the compound (A).

| | |
|---|---|
| C10H21—O-Ph-Ph-COO-Ph(OH)—CO—C*H(CH3)—C2H5 | 67 wt % |
| C12H25—O-Ph-COO-Ph-O—CH2—C*H(CH3)—C2H5 | 33 wt % |

Two glass plates having transparent electrodes were coated with polyimide films which were rubbed in a given direction. The two glass plate were placed in face-to-face relationship with the rubbing direction of the polyimide films being oriented in the parallel direction to form a liquid crystal cell while using glass beads (Diameter: 2 microns) as the spacers. The liquid crystal composition described above was introduced in the cell to facbricate a liquid crystal element. The liquid crystal element was placed between two polarizers placed to have the polarization directions crossing with each other. When an electric voltage of ±10 volts was applied at a temperature of 25° C., change in intensity of the transmitting light was observed. The response time was determined by measuring the change in intensity of the transmitting light to find that the response time was 420 microseconds. The spontaneous polarization (Ps) at 20° C. was 50 nC/cm$^2$.

EXAMPLE 50

A liquid crystal element was fabricated and subjected to test similarly as in Example 49, except that the used liquid crystal composition was composed of a mixture of the compound of Example 11 and the compound (B) mixed in a ratio of 50/50 by weight. The change in intensity of the transmitting light was measured when an electric voltage of ±10 volts was applied. The response time was 40 microseconds at 35° C., 55 microseconds at 30° C. and 70 microseconds at 25° C. The spontaneous polarization (Ps) at 25° C. was 20 nC/cm$^2$.

EXAMPLE 51

A liquid crystal element was fabricated and subjected to test similarly as in Example 49, except that the used liquid crystal composition was composed of the liquid crystal composition as described in Example 46. The change in intensity of the transmitting light was measured when an electric field of ±10 volts was applied. The response time was 83 microseconds at 40° C., 145 microseconds at 35° C. and 200 microseconds at 30° C. The spontaneous polarization (Ps) at 30° C. was 40 nC/cm$^2$.

EXAMPLE 52

A liquid crystal composition was prepared by mixing liquid crystal compounds set forth below in a mixing ratio as set forth below.

| | |
|---|---|
| 2-(4-nonyloxyphenyl)-5-heptyloxypyrimidine | 33% |
| 2-(4-hexyloxyphenyl)-5-octylpyrimidine | 33% |
| 2-(4-octyloxyphenyl)-5-octyloxypyrimidine | 33% |

The prepared liquid crystal composition had a melting point of 29° C., and exhibited the smectic C phase in the temperature range of up to 69° C., exhibited the smectic A phase up to 80° C., and exhibited the nematic phase up to 86° C. The compound of Example 20 was added to the composition in an amount of 10 wt %. The composition exhibited the cholesteric phase within the temperature range of from 86° C. to 84° C., exhibited the smectic A phase within the temperature range of from 84° C. to 54° C., and exhibited the chiral smetic C phase (Sc* phase) within the temperature range of from 54° C. to the room temperature. The liquid crystal composition was introduced in a cell (Spacing between the Electrodes: 12 microns), and the composition was cooled at a rate of 0.1° C./minute to fabricate a liquid crystal element which was subjected to test. A high speed change in intensity of transmitting light was observed when an electric voltage of ±30 volts was applied.

EXAMPLE 53

A liquid crystal composition was prepared by mixing liquid crystal compounds set forth below in a mixing ratio as set forth below.

| | |
|---|---|
| 2-(4-nonyloxyphenyl)-5-heptylpyrimidine | 22.2% |
| 2-(4-hexyloxyphenyl)-5-octylpyrimidine | 22.2% |
| 2-(4-octyloxyphenyl)-5-octyloxypyrimidine | 22.2% |
| 4-pentyloxyphenyl 4-octyloxybenzoate | 7.1% |
| 4-hexyloxyphenyl 4-octyloxybenzoate | 7.1% |
| 4-hexyloxyphenyl 4-decyloxybenzoate | 7.1% |
| 4-hexyloxyphenyl 4-pentylbenzoate | 7.1% |
| Compound of Example 21 | 5.0% |

The prepared composition exhibited the chiral smectic C phase within the temperature range of from −3.6° C. to 42° C., exhibited the smectic A phase within the temperature range of from 42° C. to 66° C. and exhibited the cholesteric phase within the temperature range of from 66° C. to 77.5° C.

The liquid crystal composition was introduced in a cell (Spacing between the Electrodes: 4 microns) to fabricate a liquid crystal element which was subjected to test. Change in intensity of transmitting light was observed when an electric voltage of ±10 volts was applied. The response time was 770 microseconds at 25° C.

EXAMPLE 54

A liquid crystal composition was prepared by mixing liquid crystal compounds set forth below in a mixing ratio as set forth below.

| | |
|---|---|
| 2-(4-nonyloxyphenyl)-5-heptyloxypyrimidine | 31.7% |
| 2-(4-hexyloxyphenyl)-5-octylpyrimidine | 31.7% |
| 2-(4-octyloxyphenyl)-5-octyloxypyrimidine | 31.7% |
| Compound of Example 24 | 4.9% |

The thus prepared composition exhibited the chiral smectic C phase within the temperature range of from 12° C. to 59° C., exhibited the smectic A phase within the temperature range of from 59° C. to 82° C. and exhibited the cholesteric phase within the temperature range of from 82° C. to 86.5° C.

The liquid crystal composition was introduced in a cell (Spacing between the Electrodes: 4 microns) to fabricate a liquid crystal element which was subjected to test. Change in intensity of transmitting light was observed when an electric voltage of ±10 volts was applied.

EXAMPLE 55

The compound of Example 10 was introduced in a cell (Spacing between the Electrodes: 2 microns) to fabricate a liquid crystal element which was subjected to test. Change in intensity of transmitting light was observed when an electric voltage of ±10 volts was applied to find that the response time was 50 microseconds at 92° C.

EXAMPLE 56

The compound of Example 13 and the compound set forth below were mixed to prepare a liquid crystal composition.

| | |
|---|---|
| n-$C_{10}H_{21}$—O-Ph-COO-Ph(OH)—CO—$C^*H(CH_3)$—$C_2H_5$ | 5.7 wt % |
| $C_{11}H_{23}$—O-Ph-COO-Ph-O—$C_6H_{13}$ | 94.3 wt % |

The phase transition temperatures of the thus prepared composition were Cr 47 Sc* 77 SA 88N 91° C. I. The spontaneous polarization (Ps) at 57° C. was 1.85 nC/cm$^2$.

EXAMPLE 57

The compound of Example 6 and the compound set forth below were mixed to prepare a liquid crystal composition.

| | |
|---|---|
| n-$C_{10}H_{21}$—O-Ph-COO-Ph-CO—$C^*H(CH_3)$—$C_2H_5$ | 5 wt % |
| $C_{11}H_{23}$—O-Ph-COO-Ph-O—$C_6H_{13}$ | 95 wt % |

The phase transition temperatures of the thus prepared composition were Cr 50 Sc* 76 SA 90N 92° C. I. The spontaneous polarization (Ps) at 56° C. was 2.0 nC/cm$^2$.

EXAMPLE 58

A liquid crystal composition was prepared by mixing liquid crystal compounds set forth below in a mixing ratio as set forth below.

| | |
|---|---|
| 2-(4-nonyloxyphenyl)-5-heptyloxypyrimidine | 31.5% |
| 2-(4-hexyloxyphenyl)-5-octylpyrimidine | 31.5% |
| 2-(4-octyloxyphenyl)-5-octyloxypyrimidine | 31.5% |
| Compound of Example 41 | 5.5% |

The thus prepared liquid crystal composition exhibited the chiral smectic C phase in the temperature range of from 5° C. to 43° C., exhibited the smectic A phase within the temperature range of from 43° C. to 83° C. and exhibited the cholesteric phase within the temperature range of from 83° C. to 86° C.

The liquid crystal composition was introduced in a cell (Spacing between the Electrodes: 10 microns) to fabricate a liquid crystal element which was subjected to test. A change in intensity of transmitting light was observed when an electric voltage of ±25 volts was applied and the transmitting light was observed through a polarizing microscope. The response time was 420 microseconds at 33° C. The spontaneous polarization (Ps) of the element was 2.9 nC/cm$^2$ at 33° C.

EXAMPLE 59

A liquid crystal composition was prepared by mixing liquid crystal compounds set forth below in a mixing ratio as set forth below.

| | |
|---|---|
| 2-(4-nonyloxyphenyl)-5-heptyloxypyrimidine | 30.0% |
| 2-(4-hexyloxyphenyl)-5-octylpyrimidine | 30.0% |
| 2-(4-octyloxyphenyl)-5-octyloxypyrimidine | 30.0% |
| Compound of Example 42 | 10.0% |

The prepared liquid crystal composition exhibited the chiral smectic C phase in the temperature range of from 10° C. to 50° C., exhibited the smectic A phase within the temperature range of from 50° C. to 82.5° C. and exhibited the cholesteric phase within the temperature range of from 82.5° C. to 85° C. The liquid crystal composition was introduced in a cell (Spacing between the Electrodes: 10 microns) to fabricate a liquid crystal element which was subjected to test. A change in intensity of transmitting light was observed when an electric voltage of ±25 volts was applied and the transmitting light was observed through a polarizing microscope. The response time was 340 microseconds at 40° C.

EXAMPLE 60

A liquid crystal composition was prepared by mixing liquid crystal compounds set forth below in a mixing ratio as set forth below.

| | |
|---|---|
| 2-(4-nonyloxyphenyl)-5-heptyloxypyrimidine | 31.7% |
| 2-(4-hexyloxyphenyl)-5-octylpyrimidine | 31.7% |
| 2-(4-octyloxyphenyl)-5-octyloxypyrimidine | 31.7% |
| Compound of Example 40 | 4.9% |

The prepared liquid crystal composition exhibited the chiral smectic C phase in the temperature range of from 4° C. to 59° C., exhibited the smectic A phase within the temperature range of from 59° C. to 75° C. and exhibited the cholesteric phase within the temperature range of from 75° C. to 82° C.

EXAMPLE 61

A liquid crystal composition was prepared by mixing liquid crystal compounds set forth below in a mixing ratio as set forth below.

| | |
|---|---|
| 2-(4-nonyloxyphenyl)-5-heptylpyrimidine | 28.3% |
| 2-(4-hexyloxyphenyl)-5-octylpyrimidine | 28.3% |
| 2-(4-octyloxyphenyl)-5-nonylpyrimidine | 28.3% |
| Compound of Example 10 | 7.6% |
| 4-(4'-octyloxy)diphenyl 4-2-(methylbutyl)bonzoate (n-C$_8$H$_{17}$—O-Ph-Ph-OCO-Ph-CH$_2$—C*H(CH$_3$)—C$_2$H$_5$ | 7.5% |

The thus prepared liquid crystal composition exhibited the cholesteric phase in the temperature range of from 77° C. to 71° C., exhibited the smectic A phase within the temperature range of from 71° C. to 46° C. and exhibited the chiral smectic C phase within the temperature range of from 46° C. to 1° C.

The liquid crystal composition was introduced in a cell (Spacing between the Electrodes: 2 microns) to fabricate a liquid crystal element which was subjected to test. A change in intensity of transmitting light was observed when an electric voltage of ±10 volts was applied and the transmitting light was observed through a polarization microscope. The response time was 300 microseconds at 30° C.

EXAMPLE 62

A liquid crystal composition was prepared by mixing liquid crystal compounds set forth below in a mixing ratio as set forth below.

| | |
|---|---|
| 2-(4-nonyloxyphenyl)-5-heptylpyrimidine | 26.6% |
| 2-(4-hexyloxyphenyl)-5-octylpyrimidine | 26.6% |
| 2-(4-octyloxyphenyl)-5-nonylpyrimidine | 26.6% |
| 4-(4'Ooctyloxy)diphenyl 4-(2-methylbutyl)banzoate (n-C$_8$H$_{17}$—O-Ph-Ph-OCO-Ph-CH$_2$—C*H(CH$_3$—C$_2$H$_5$) | 10.0% |
| Compound of Example 13 | 10.2% |

The thus prepared liquid crystal composition exhibited the cholesteric phase in the temperature range of from 69° C. to 64° C., exhibited the smectic A phase within the temperature range of from 64° C. to 39° C. and exhibited the chiral smetic C phase within the temperature range of from 39° C. to 0° C.

The liquid crystal composition was contained in a cell (Spacing between the Electrodes: 2 microns) to fabricate a liquid crystal element which was subjected to test. A change in intensity of transmitting light was observed when an electric voltage of ±10 volts was applied and the transmitting light was observed through a polarizing microscope. The response time was 160 microseconds at 30° C.

What is claimed is:

1. An optically active compound represented by the formula (I):

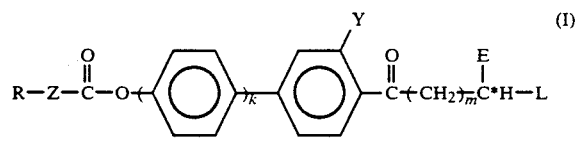

wherein R is an alkyl or alkoxy group having 4 to 22 carbon atoms; Z is

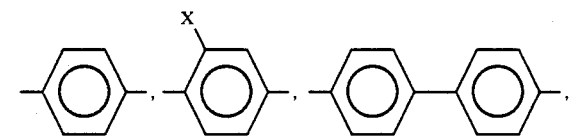

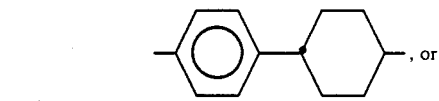

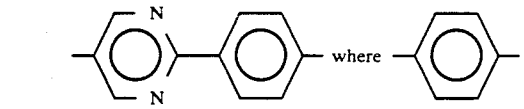

represents 1,4-phenylene group;

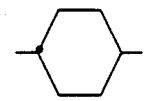

represents trans-1,4-cyclohexane group; X is a halogen atom; k is zero or 1 with the proviso that when Z is

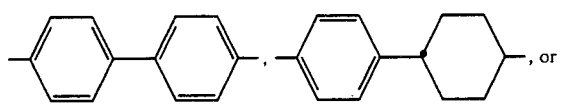 , or

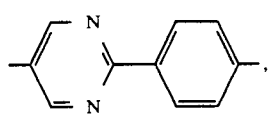 , k is zero; Y is a hydroxyl group; C* is an asymmetric carbon atom; E is a methyl group; L is an alkyl or aryl group having not more than 10 carbon atoms; and m is an integer of from 0 to 6.

2. The optically active compound according to claim 1 wherein k is zero;
E is methyl;
Y is hydroxyl;
Z is

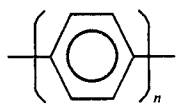

where n is 1 or 2.

3. A chiral liquid crystal composition comprising an optically active compound mixed with one or more of other liquid crystal compounds, said optically active compound being represented by the following formula (I):

$$R-Z-\overset{O}{\underset{\|}{C}}-O-\!\!\left(\!\!\bigcirc\!\!\right)_{\!k}\!\!-\!\!\bigcirc\!\!\overset{Y}{\underset{}{-}}\!\!-\overset{O}{\underset{\|}{C}}-(CH_2)_{\overline{m}}\overset{E}{\underset{|}{C^*H}}-L \quad (I)$$

wherein R is an alkyl or alkoxy group having 4 to 22 carbon atoms; Z is

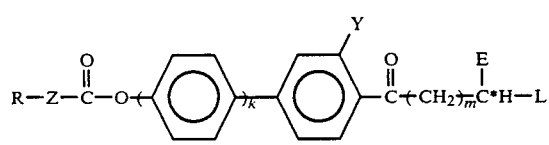

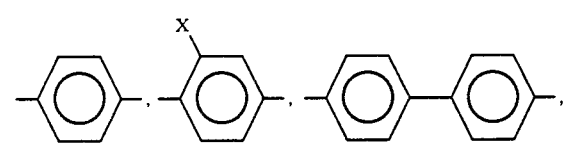

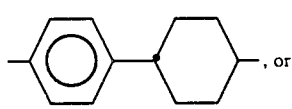 , or

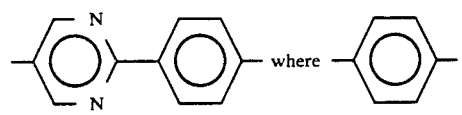 where 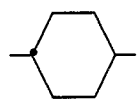

represents 1,4-phenylene group;

represents trans-1,4-cyclohexane group; x is a halogen atom; k is zero or 1 with the proviso that when k is zero, Z is

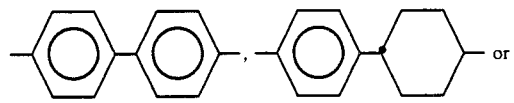

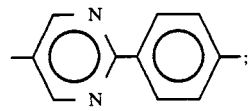 ;

i is a hydroxyl group; C* is an asymmetric carbon atom; E is methyl group; L is an alkyl or aryl group having not more than 10 carbon atoms; and m is an integer of from 0 to 6.

4. The chiral liquid crystal composition according to claim 3, wherein said other liquid crystal compounds mixed with said optically active compound represented by the formula (I) are represented by the following formulae of:

Alk—O—Ph—COO—Ph—O—Alk*,
Alk—O—Ph—COO—Ph—COO—Alk*,
Alk*—O—Ph—Ph—COO—Ph—O—Alk,
Alk*—Ph—COO—Ph—Ph—O—Alk,
Alk*—O—Ph—COO—Ph—COO—Ph—O—Alk,
  wherein Ph is a 1,4-substituted phenylene group,
  Ph—Ph is a 4,4'-substituted diphenylene group, Alk is an alkyl group having 6 to 14 carbon atoms, and Alk* is an optically active alkyl group having 4 to 10 carbon atoms.

5. The chiral liquid crystal composition according to claim 3, wherein said other liquid crystal compounds mixed with said optically active compound represented by the formula (I) are represented by the following formulae of:

Alk—O—Ph—COO—Ph—O—Alk',
Alk—O—Ph—COO—Ph—Alk',
Alk—Py—Ph—O—Alk',
Alk—O—Py—Ph—O—Alk'
  wherein Ph is a 1,4-substituted phenylene group,
  Py is a 2,5-substituted pyrimidine group

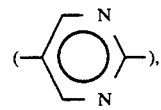 ,

Alk is an alkyl group having 4 to 10 carbon atoms, and Alk' is an alkyl group having 4 to 10 carbon atoms.

6. The chiral liquid crystal composition according to claim 3, wherein said other first liquid crystal compounds mixed with said optically active compound represented by the general formula (I) are represented by the following formulae of:

Alk—O—Ph—COO—Ph—Alk*,
Alk—O—Ph—COO—Ph—COO—Alk*,
Alk*—O—Ph—Ph—COO—Ph—O—Alk,

Alk*—Ph—COO—Ph—Ph—O—Alk, and

Alk*—O—Ph—COO—Ph—COO—Ph—O—Alk wherein Alk is an alkyl group having 6 to 14 carbon atoms, Alk* is an optically active alkyl group having 4 to 10 carbon atoms, Ph is a 1,4-substituted phenylene group and Ph—Ph is a 4,4'-substituted diphenylene group; and further said other second liquid crystal compounds mixed with said optically active compound represented by the general formula (I) are represented by the following formulae of:

Alk—O—Py—Ph—Alk' and

Alk—O—Py—Ph—O—Alk' wherein Alk is an alkyl group having 4 to 10 carbon atoms, Alk' is an alkyl group having 4 to 10 carbon atoms, Ph is a 1,4-substituted phenylene group, and Py is a 2,5-substituted pyrimidine ring.

7. The chiral liquid crystal composition according to claim 3 wherein k is zero;

E is methyl;

Y is hydroxyl;

Z is

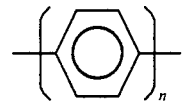

where n is 1 or 2.

* * * * *